(12) United States Patent
Bray et al.

(10) Patent No.: US 7,410,458 B2
(45) Date of Patent: Aug. 12, 2008

(54) BRACHYTHERAPY IMPLANT SEEDS

(75) Inventors: Lane A. Bray, Richland, WA (US); David J. Swanberg, Kennewick, WA (US); James L. Madsen, Richland, WA (US); Jay Draper, Kennewick, WA (US); Garrett N. Brown, Krum, TX (US); Matthew J. Bales, Kennewick, WA (US); Donald C. Lawrence, deceased, late of San Jose CA (US); by Karen Thompson, legal representative, San Jose, CA (US)

(73) Assignee: IsoRay Medical, Inc., Richland, WA (US)

(*) Notice: Subject to any disclaimer, the term of this patent is extended or adjusted under 35 U.S.C. 154(b) by 754 days.

(21) Appl. No.: 10/712,820

(22) Filed: Nov. 12, 2003

(65) Prior Publication Data

US 2005/0101826 A1 May 12, 2005

(51) Int. Cl.
*A61N 5/00* (2006.01)
(52) U.S. Cl. .............................................. 600/8
(58) Field of Classification Search ............. 600/1–8; 424/1.29, 1.61
See application file for complete search history.

(56) References Cited

U.S. PATENT DOCUMENTS

| | | | |
|---|---|---|---|
| 1,753,287 A | 4/1930 | Failla | |
| 3,351,049 A | 11/1967 | Lawrence | |
| 3,706,689 A | 12/1972 | Haskins | 252/301.1 R |
| 4,323,055 A | 4/1982 | Kubiatowicz | |
| 4,702,228 A | 10/1987 | Russell, Jr. et al. | |
| 4,784,116 A | 11/1988 | Russell, Jr. et al. | |
| 4,891,165 A | 1/1990 | Suthanthiran | |
| 4,994,013 A | 2/1991 | Suthanthiran et al. | |
| 5,071,610 A | 12/1991 | Hagan et al. | 264/120 |
| 5,163,896 A | 11/1992 | Suthanthiran et al. | |
| 5,342,283 A | 8/1994 | Good | |
| 5,368,736 A | 11/1994 | Horwitz et al. | 210/635 |
| 5,405,309 A | 4/1995 | Carden, Jr. | |
| 5,512,256 A | 4/1996 | Bray et al. | 423/2 |

(Continued)

FOREIGN PATENT DOCUMENTS

JP          01-254900          10/1989

(Continued)

OTHER PUBLICATIONS

3M Empore™ Rad Disks Product Listing, 1998. Available at http://www.mmm.com/empore, downloaded Mar. 11, 2004.

(Continued)

*Primary Examiner*—John P Lacyk
(74) *Attorney, Agent, or Firm*—Seed IP Law Group PLLC (57) ABSTRACT

This invention includes methods of fabricating brachytherapy implant seeds, methods of fabricating brachytherapy implant seed cores, and brachytherapy implant seeds independent of method of fabrication. In one implementation, a brachytherapy implant seed includes a sealed inorganic metallic cylinder having a radioactive core received therein. The radioactive core includes an inorganic amorphous silicate glass tube having an exterior surface extending axially along the tube. An inorganic crystalline ceramic coating is received on at least a portion of the inorganic amorphous glass tube exterior surface. The coating includes a therapeutic dose of radioactive material. A radiographic marker is received within the sealed inorganic metallic cylinder. Other aspects and implementations are contemplated.

28 Claims, 7 Drawing Sheets

U.S. PATENT DOCUMENTS

| | | | |
|---|---|---|---|
| 5,683,345 | A | 11/1997 | Waksman et al. |
| 5,749,042 | A | 5/1998 | Bray et al. ............... 423/2 |
| 5,899,882 | A | 5/1999 | Waksman et al. |
| 6,060,036 | A | 5/2000 | Armini |
| 6,066,302 | A | 5/2000 | Bray |
| 6,099,457 | A | 8/2000 | Good |
| 6,099,458 | A | 8/2000 | Robertson |
| 6,139,749 | A | 10/2000 | Goken et al. ............... 210/651 |
| 6,306,074 | B1 | 10/2001 | Waksman et al. |
| 6,309,614 | B1 | 10/2001 | Horwitz et al. ............... 423/2 |
| 6,351,049 | B1 | 2/2002 | Chassoulier et al. |
| 6,403,916 | B1 | 6/2002 | Spooner et al. |
| 6,455,024 | B1 * | 9/2002 | Glajch et al. ............... 424/1.33 |
| 6,458,070 | B1 | 10/2002 | Waksman et al. |
| 6,471,632 | B1 | 10/2002 | Jahrmarkt et al. |
| 6,479,920 | B1 | 11/2002 | Lal et al. ............... 310/309 |
| 6,485,406 | B1 | 11/2002 | Ziegler et al. |
| 6,503,185 | B1 | 1/2003 | Waksman et al. |
| 6,554,756 | B1 | 4/2003 | Schaart |
| 6,589,502 | B1 | 7/2003 | Coniglione et al. ........ 424/1.25 |
| 6,608,227 | B1 | 8/2003 | Spooner et al. |
| 6,666,811 | B1 | 12/2003 | Good |
| 6,689,043 | B1 | 2/2004 | McIntire et al. |
| 6,749,554 | B1 | 6/2004 | Snow et al. |
| 6,821,242 | B1 | 11/2004 | Waksman et al. |
| 2002/0022781 | A1 | 2/2002 | McIntyre et al. |
| 2002/0162828 | A1 | 11/2002 | Spooner et al. |
| 2003/0088146 | A1 | 5/2003 | Slater et al. ............... 600/8 |
| 2003/0092959 | A1 | 5/2003 | Slater et al. ............... 600/8 |
| 2003/0229259 | A1 | 12/2003 | Waksman et al. |
| 2004/0076579 | A1 | 4/2004 | Coniglione et al. ........ 424/1.11 |
| 2004/0097779 | A1 | 5/2004 | McIntyre et al. |
| 2004/0192999 | A1 | 9/2004 | Waksman et al. |
| 2004/0236169 | A1 | 11/2004 | Slater et al. ............... 600/8 |
| 2004/0242953 | A1 | 12/2004 | Good |

FOREIGN PATENT DOCUMENTS

| | | |
|---|---|---|
| WO | WO 00/51136 | 8/2000 |
| WO | WO 01/80251 | 10/2001 |
| WO | WO 2004/053892 | 6/2004 |

OTHER PUBLICATIONS

Balmer, M.L. et al., "New Silicotitanate Waste Forms: Development and Characterization," Interfacial and Processing Sciences Annual Report 1999. Available at http://www.pni.gov/microcats/aboutus/publications/microsystems/annual_report1999. Downloaded Sep. 19, 2004.

Cary, A., "PNNL gel may charge drug obstacles," *Tri-City Herald*, Mar. 30, 2001. Available at http://www.tri-cityherald.com. Downloaded Oct. 8, 2004.

Harper, P.V. et al., "Isotopes Decaying by Electron Capture: a New Modality in Brachytherapy," in *Proceedings of the International Conference on the Peaceful Uses of Atomic Energy*, Geneva Switzerland, 1958, pp. 417-422.

Henschke, U.K. et al., "Cesium-131 Seeds for Permanent Implants," *Radiology* 85(6): 1117-1119, Dec. 1965.

Hobbs, D.T., "Strategic Design and Optimization of Inorganic Sorberts for Cesium, Strontium, and Actinides," Westinghouse Savannah River Company Report WSRC-RP-2002-00337. Available at http://www.osti.gov/bridge. Downloaded Oct. 5, 2005.

Hodgman, C.D. (ed.), *"Handbook of Chemistry and Physics, 31st edition,"* Chemical Rubber Publishing Co., Cleveland, OH, pp. 408-409, 1949.

Hodgman, C.D. (ed.), *"Handbook of Chemistry and Physics, 31st edition,"* Chemical Rubber Publishing Co., Cleveland, OH, pp. 524-525, 1949.

Kraus and Nelson, "Anion Exchange Studies of the Fission Products," in *Proc. Int. Conf. Peaceful Uses of Atomic Energy*, vol. 7, Geneve, 1955, pp. 113-125.

Kurath, D.E. et al., "Ion Exchange Removal of Cesium from Simulated and Actual Hanford Tanks 241-SY-101 and 241-SY-103," in *Proceedings of the International Topical Meeting on Nuclear and Hazardous Waste Management Spectrum '96*, Aug. 18-23, 1996, Seattle, Washington, American Nuclear Society, La Grange Park, IL, 1996, pp. 222-228.

Naumann, R.A. et al., "Preparation of Radioactive Targets for Charged-Particle Nuclear Spectroscopy at the CERN-ISOLDE Project," *Nuclear Instruments and Methods in Physics Research B 26*: 59-64, 1987.

pSiVida Company, BioSilicon internet web pages. Available at http://www.psivida.com.au/text. Downloaded Nov. 3, 2004.

Smith, L.L. et al., "Application of Empore™ Strontium Rad Disks to the Analysis of Radiostrontium in Environmental Water Samples," *Radiochimica Acts* 73:165-170, 1996.

Wike, J.S. et al., "Chemistry for Commercial Scale Production of Yttrium-90 for Medical Research," *International Journal of Radiation Applications and Instrumentation Part A*, 41(9): 861-865, 1990.

Willard and Goodspeed, "Separation of Strontium, Barium, and Lead from Calcium and Other Metals," *Industrial and Engineering Chemistry* 8(6):414-418, 1936.

PCT/US2004/029477; Filed Sep. 8, 2004; Search Report; 6 pps.

"Radiation protection—Sealed radioactive sources—Leakage test methods", International Standard, ISO 9978:1992(E), First Edition, Feb. 15, 1992.

"Radiation protection—Sealed radioactive sources—General requirements and classification", International Standard, ISO 2919:1999(E), Second Edition, Feb. 15, 1999.

R. Braun et al., "Crystalline Silicotitanates—Novel Commercial Cesium Ion Exchangers", UOP, pp. 1-12, pre-Nov. 2003.

Heintz et al., *Comparison of I-125 sources used for permanent interstitial implants*, 28 Med. Phys., No. 4, pp. 671-682 (Apr. 2001).

Korb et al., *Modern Brachytherapy for Localized Prostate Cancer : The Northwest Hospital (Seattle) Experience*, 3 Reviews in Urology, No. 1, pp. 51-60 (Winter 2001).

* cited by examiner

BRACHYTHERAPY IMPLANT SEEDS

TECHNICAL FIELD

This invention relates to methods of fabricating brachytherapy implant seeds, to methods of fabricating brachytherapy implant seed cores, and to brachytherapy implant seeds independent of method of fabrication.

BACKGROUND OF THE INVENTION

Radiation therapy (radiotherapy) refers to the treatment of diseases, primarily but not limited to the treatment of tumors such as cancer, with radiation. Radiotherapy is used to destroy malignant or unwanted tissue without causing excessive damage to the nearby healthy tissues.

Ionizing radiation can be used to selectively destroy cancerous cells contained within healthy tissue. Malignant cells are normally more radiosensitive than healthy cells. Therefore, by applying radiation of the correct amount over the ideal time period, it is possible to destroy all of the undesired cancer cells while saving or minimizing damage to the healthy tissue. For many decades, localized cancer has often been cured by the application of a carefully determined quantity of ionizing radiation during an appropriate period of time. Various methods have been developed for irradiating cancerous tissue while minimizing damage to the nearby healthy tissue. Such methods include the use of high-energy radiation beams from linear accelerators and other devices designed for use in external beam radiotherapy.

Another method of radiotherapy includes brachytherapy. Here, substances in the form of seeds, needles, wires or catheters are implanted permanently or temporarily directly into/near the cancerous tumor. Radioactive materials used include radon, radium and iridium-192. More recently, the radioactive isotopes cesium-131, iodine-125 and palladium-103 have been used. Examples are described in U.S. Pat. Nos. 3,351,049; 4,323,055; and 4,784,116, which are incorporated herein by reference.

During the last 30 years, over 100 papers (both scientific and lay publications) have been published on the use of iodine-125 and palladium-103 in treating slow growth prostate cancer. Despite the demonstrated success of iodine-125 and palladium-103, there are certain disadvantages and limitations in their use. While the total dose can be controlled by the quantity and spacing of the seeds, the dose rate is set by the half-life of the radioisotope (60 days for I-125 and 17 days for Pd-103). For use in faster growing tumors, the radiation should be delivered to the cancerous cells at a faster, more uniform rate, while simultaneously preserving all of the advantages of using a soft X-ray emitting radioisotope. Such cancers are those found in the brain, lung, pancreas, prostate and other tissues.

The low energy X-ray seeds of I-125 and Pd-103 have been used successfully in the treatment of cancer. Methods for encapsulation of these radioactive isotopes as seeds or capsules for interstitial brachytherapy are described in U.S. Pat. Nos. 1,753,287; 3,351,049; 4,323,055; 4,702,228; 4,784,116; 4,891,165; 4,994,013; 5,163,896; 5,405,309 and 6,099,458, and are incorporated herein by reference.

Some of the above-referenced seeds suffer from a number of disadvantages and limitations. They include: (a) the lower energy of the X-ray from Pd-103 (20 key); (b) the half-life of the I-125 seed (60-days) is typically too long to permit its use as a permanent implant in anything other than slow growing tumors; (c) the use of a silver wire marker incorporated into I-125 seeds (U.S. Pat. No. 4,323,005) has a large unwanted amount of characteristic low energy (<10 keV) silver K-X-rays; and (d) seeds with various internal components with non-optimized geometries, which require a greater amount of isotope to compensate for the non-uniform dose pattern surrounding the seed.

The use of sealed radioactive sources became so widespread that standards used for production were established for radiation protection. Leakage test methods for sealed radioactive sources continue to be refined (ISO 9978:1992(E) and ISO 2919:1999(E)). In order to meet these standards, the sealed seeds must be exposed to various environmental stresses while remaining completely sealed. The most difficult test to pass is the impact test, which requires that the metal seed body be placed on a steel anvil, and that a 2.54 cm diameter, 50 gram weight be dropped on the seed from a height of 1 meter. Even though the typical titanium cased seed can is then flattened, there must be no leakage from the metal seed body. To pass this stringent test, seed manufacturers (e.g., in constructions such as in prior art such as U.S. Pat. Nos. 4,702,228; 4,784,116; 4,891,165; 5,405,309, etc.) incorporate thick end welds, thick end caps and/or massive internal components in order to retain the original cylindrical shape. However, these characteristics can result in non-uniform dosimetric patterns around the seed due to the self-absorption of the radiation. This non-isotropic dose increases the probability that cancer cells residing in this shadowed low dose area will survive and give rise to a return of the cancer at a later date.

Several prior art seed designs (U.S. Pat. Nos. 3,351,049; 4,994,013; and 5,163,896) suggest the use of plastics, a multitude of ion exchange resin types (nylon, cellulose ester or acetate binders, or rubber) to capture and hold the radioactive material. With increasing concentrations of radioisotopes, unacceptable gas pressure (e.g., $H_2$, $CO$, $CO_2$, $CH_4$, etc.) may be generated by the autoradiolysis of organic materials within the cavity of the seed. Release of radioactive material due to a breach in the seed can by over-pressurization is a risk.

While the invention was motivated in addressing at least some of the above issues, it is in no way so limited. The invention is only limited by the accompanying claims as literally worded, without interpretative or other limiting reference to the specification, and in accordance with the doctrine of equivalents.

SUMMARY

The invention comprises methods of fabricating brachytherapy implant seeds, methods of fabricating brachytherapy implant seed cores, and brachytherapy implant seeds independent of method of fabrication. In one implementation, a brachytherapy implant seed includes a sealed inorganic metallic cylinder having a radioactive core received therein. The radioactive core includes an inorganic amorphous silicate glass tube having an exterior surface extending axially along the tube. An inorganic crystalline ceramic coating is received on at least a portion of the inorganic amorphous glass tube exterior surface. The coating includes a therapeutic dose of radioactive material. A radiographic marker is received within the sealed inorganic metallic cylinder.

In one implementation, a method of fabricating a brachytherapy implant seed comprises providing an inorganic amorphous silicate glass tube having an exterior surface extending axially along the tube. At least a portion of the tube exterior surface is coated with ceramic precursors. After the coating, the ceramic precursors are exposed to a temperature effective to form a continuous inorganic crystalline ceramic coating from the precursors over the tube exterior surface portion.

After the exposing, a therapeutic dose of radioactive material is sorbed onto the ceramic coating. At least a portion of the ceramic coated glass tube with therapeutic dose of radioactive material is provided within an inorganic metallic cylinder. An inorganic metallic cap is welded onto an end of the inorganic metallic cylinder having the portion of the ceramic coated glass tube with therapeutic dose of radioactive material therein.

In one implementation, a method of fabricating a brachytherapy implant seed core comprises providing a tube having an exterior surface extending axially along the tube. A vessel is provided which comprises a die passageway sized to slideably receive the tube therethrough to form a coating onto the tube exterior surface. A mixture of ceramic precursors is provided within the vessel. The tube is moved into the ceramic precursor mixture within the vessel and through the die passageway to out of the vessel effective to form a coating of the ceramic precursors onto the tube exterior surface. The ceramic precursor coating is exposed to a temperature effective to form an inorganic crystalline ceramic coating over the tube exterior surface portion. After such exposing, a therapeutic dose of radioactive material is sorbed onto the ceramic coating.

In one implementation, a method of fabricating a brachytherapy implant seed core comprises providing a tube having an exterior surface extending axially along the tube. A mold is provided which comprises a mold cavity sized to receive the tube and form a coating thereover. A mixture of ceramic precursors is inserted to within the mold cavity. The tube is inserted to within the mold cavity. An adherent coating of the ceramic precursors is formed onto the tube exterior surface within the mold cavity. After such forming, the mold is destructively melted. After the melting, the ceramic precursor coating is exposed to a temperature effective to form an inorganic crystalline ceramic coating over the tube exterior surface. After such exposing, a therapeutic dose of radioactive material is sorbed onto the ceramic coating.

In one implementation, a method of fabricating a brachytherapy implant seed comprises providing an inorganic metallic cylinder. An inorganic metallic cap is welded onto an end of the inorganic metallic cylinder. The welding comprises firing a series of laser pulses towards the cap and cylinder while rotating the cap and cylinder effective to form, a series of overlapping welds. In one implementation, adjacent welds overlap one another by no more than 50% calculated as weld diameter overlap divided by weld diameter. In one implementation, the laser pulses are fired towards the cap and cylinder at a firing angle from perpendicular to an outer surface of the metallic cylinder. A radioactive core is provided within the inorganic metallic cylinder. The radioactive core comprises a therapeutic dose of radioactive material.

Other aspects and implementations are contemplated.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In accordance with preferred aspects of the invention, a preferred embodiment brachytherapy implant seed is initially described with reference to FIG. 1, and is indicated generally with reference numeral 10. In the context of this document, a "brachytherapy implant seed" is any solid object to be permanently or temporarily implanted for imparting a radiation dose regardless of exterior form, for example regardless of whether being needle-like, capsule-like, pellet-like, etc. Implant seed 10 comprises a sealed inorganic metallic cylinder 12 having a radioactive core 14 received therein. Exemplary preferred materials for cylinder 12 are elemental or alloy titanium. However, any existing or yet-to-be developed metal or alloy is contemplated, preferably metals having a low atomic number and a high strength-to-weight ratio.

One preferred embodiment cylinder 12 comprises a cylindrical section 16 and a pair of opposing end caps 18 and 20. Components 16, 18 and 20 are preferably comprised of the same material, with caps 18 and 20 being welded to cylindrical section 16. Exemplary preferred methods of fabrication are described subsequently. An exemplary preferred length for cylindrical section 16 is from 1.0 mm to 10.0 mm. An exemplary preferred thickness for the wall of section 16 is from 0.05 mm to 0.1 mm. An exemplary preferred outside diameter, or maximum cross-dimension, of cylinder 12 is from 0.1 mm to 2.0 mm. A preferred thickness range for caps 18 and 20 is also from 0.05 mm to 0.1 mm, with the caps preferably having a diameter or maximum cross-dimension which is slightly larger than that of cylindrical section 16. Caps 18 and 20 are preferably adhered to cylindrical section 16 by welding in a preferred manner to be described subsequently. Preferably, a uniform wall thickness of components 18, 16 and 20 is utilized for cylinder construction 12.

The illustrated preferred cylinder 12 is in the form of a hermetically sealed right cylinder having substantially flat ends. Flat ends. are preferred in providing an advantage of being able to stabilize the seed after being placed in position in the tumor or other tissue, as compared to implant seeds having rounded ends. Further, rounded ends have been known to jam in the needles during loading. Regardless, seeds having other than flat ends are also, of course, contemplated. One preferred embodiment example for cylinder construction 12 is a titanium right cylinder tube having a length of 4.3 mm, an inner diameter of 0.7 mm and an outer diameter of 0.8 mm, with end caps welded thereto having a thickness of 0.1 mm.

Radioactive core 14 comprises an inorganic amorphous silicate glass tube 22. Such tube can be considered as having longitudinally opposing ends 27 which, in the FIG. 1 embodiment, are open. Tube 22 also has an exterior surface 24, an interior surface 26 extending axially along the tube, and end surfaces 28. By way of example only, preferred silicate glasses are borosilicate glasses, phosphosilicate glasses, borophosphosilicate glasses, and quartz glasses. Further by way of example only, any boron or phosphorous doping of such silicate glasses is preferably in the range of from 3 weight percent to 12 weight percent. Regardless, the glass is preferably of a material that is highly transmissive of the therapeutic radiation. An exemplary preferred length for tube 22, is from 1.0 mm to 10.0 mm. An exemplary preferred outside diameter range for tube 22 is from 0.4 mm to 2.0 mm, with an exemplary preferred inside diameter range being from 0.25 mm to 1.8 mm. A specific exemplary embodiment is a glass tube having a 0.4 mm outer diameter, a 0.3 mm inner diameter and a 4 mm to 4.25 mm length.

An inorganic crystalline ceramic coating 30 is received on at least a portion of inorganic amorphous glass tube exterior surface 24. In the exemplary depicted FIG. 1 embodiment, coating 30 coats all of tube exterior surface 24. The inorganic crystalline ceramic coating can have a thickness that is the same, greater than, or less than that of the inorganic amorphous silicate glass tube, with the exemplary FIG. 1 embodiment depicting the thickness of coating 30 being greater than that of glass tube 22. Regardless, an exemplary preferred thickness range for coating 30 is from 0.1 mm to 0.4 mm, with a specific exemplary thickness being 0.15 mm.

Exemplary preferred materials for inorganic crystalline ceramic coating 30 include metal silicates, for example aluminosilicates such as sodium aluminosilicate. In addition therewith or in substitution therefor, exemplary additional materials include silicates and oxides of aluminum, sodium, magnesium, potassium, calcium and lithium. Additionally, the preferred ceramic material 30 preferably is inherently chemically adsorptive or absorptive of one or more specific radionuclides or contains inorganic ion exchange material to be described subsequently.

Regardless, coating 30 comprises a therapeutic dose of radioactive material. In the particular exemplary FIG. 1 embodiment, such is depicted as comprising a radioactive isotope 32 that has been sorbed onto the outer surface of ceramic coating 30. Such material might permeate some or much of ceramic coating 30 depending on coating 30's porosity and outer surface smoothness, but is preferably received at the outermost portions of ceramic coating 30. This provides the radiochemical to be adjacent the inner surface of metallic cylinder 12, preferably minimizing the amount of self-absorption from internal components of the seed, and thereby maximizing the amount of radiation released from the seed, as well as enhancing uniform isotropy of the emitted radiation. An exemplary preferred radioactive material is cesium-131. However, any radioisotope is contemplated, whether existing or yet-to-be developed or isolated. By way of example only, examples include iodine-125, palladium-103, cesium-137, yttrium-90, strontium-90 and other radioisotopes of palladium, cobalt, silver, copper, iodine, uranium, thorium, actinium, rare earth metals and actinides. Further by way of example only, an exemplary preferred characteristic radiation emission is from 20 keV to 100 keV, with a specific example being 29 keV. Further by way of example only, exemplary preferred half-lives of manufactured seed are from 8 days to 100 days.

Brachytherapy implant seed 10 further comprises a radiographic marker that is received within the sealed inorganic metallic cylinder. By way of example only, such might comprise a metal vapor deposit, a metal paste, a metal ball, a metal wire, etc. Most preferably, the radiographic marker is received within the inorganic amorphous glass tube. In the depicted FIG. 1 embodiment, a radiographic marker 34 in the form of an effectively radiopaque wire is received within inorganic amorphous glass tube 22. An exemplary preferred material is gold, and regardless, an exemplary preferred thickness range or diameter for wire 34 is from 0.1 mm to 0.4 mm, with a specific example being 0.25 mm. By way of example only, exemplary additional materials for a radiopaque marker include tungsten, rhodium, platinum, lead and tin. The radiographic marker acts as an X-ray marker to facilitate external visualization of the seed after implantation to ensure adequate placement of the seed relative to the tumor or other tissue.

Figure 1:
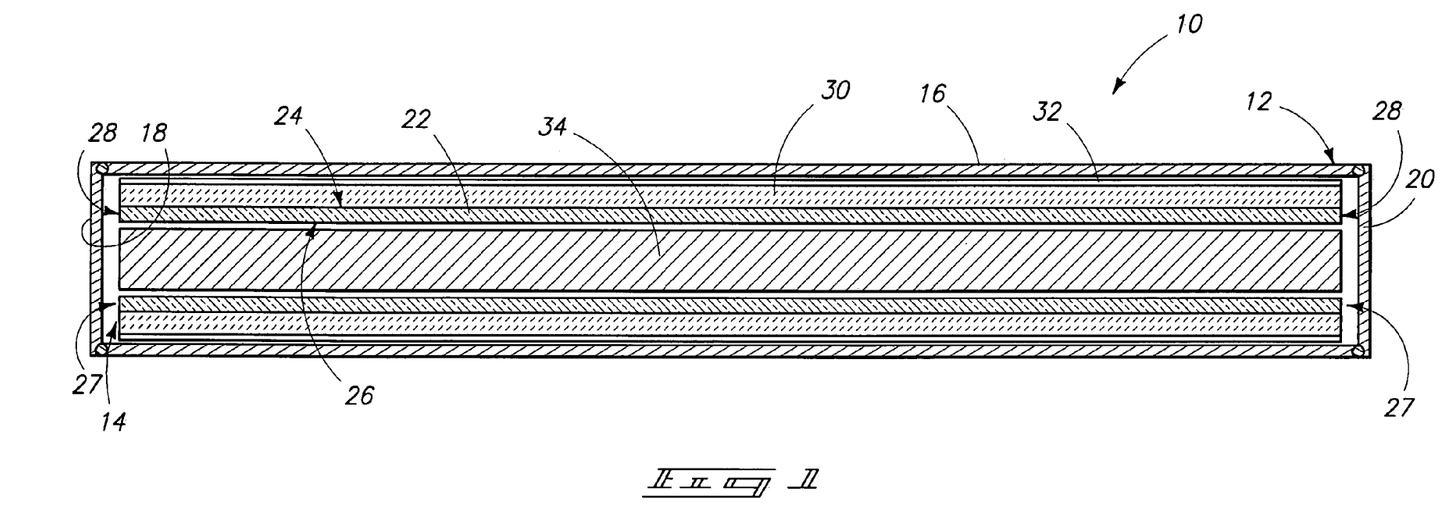
FIG. 1 is a diagrammatic sectional view of a brachytherapy implant seed in accordance with an aspect of the invention.
Figure 2:
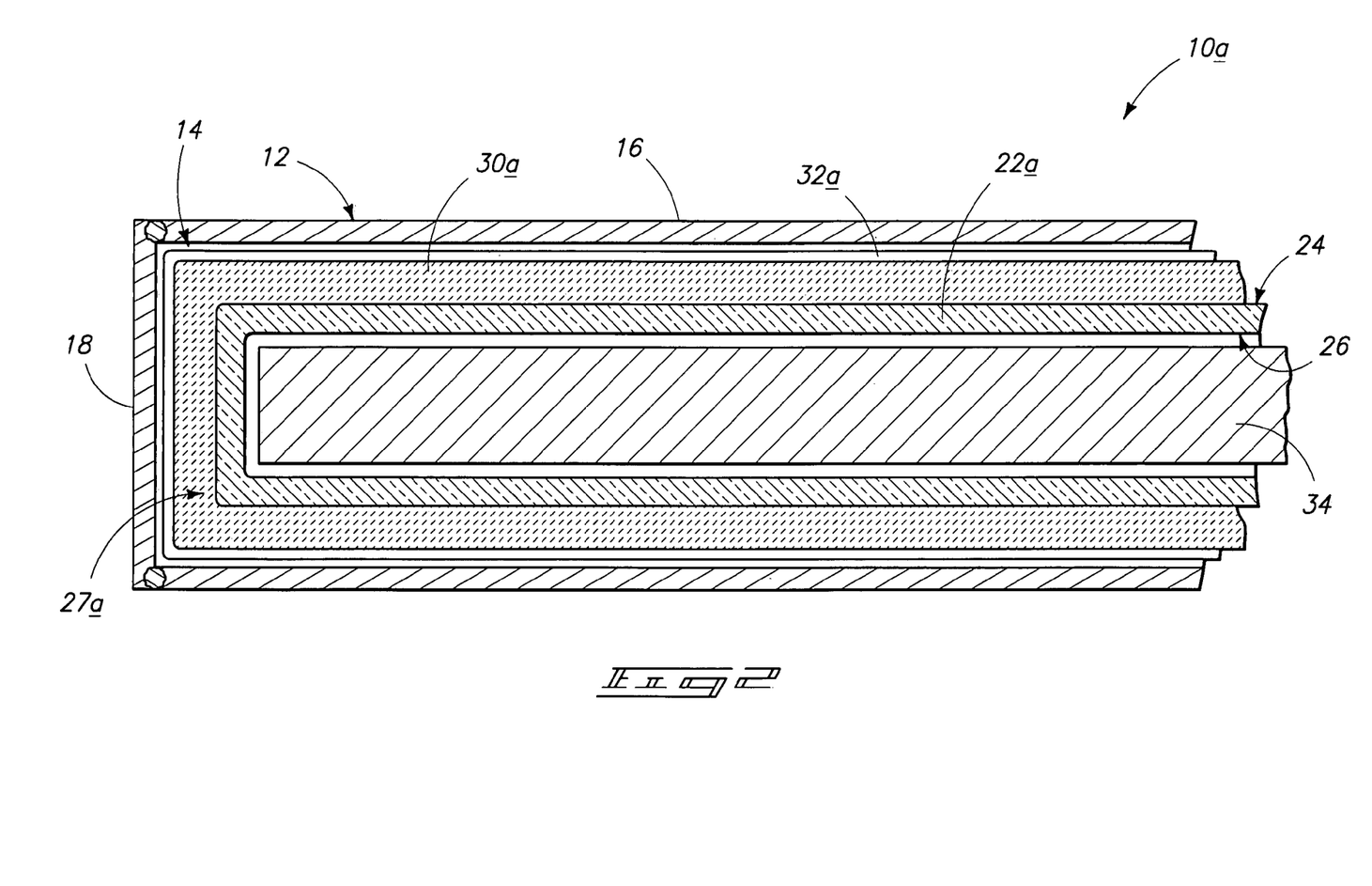
FIG. 2 is an enlarged diagrammatic sectional view of an end region of an alternate embodiment brachytherapy implant seed in accordance with an aspect of the invention.

FIG. 1 depicts a brachytherapy implant seed having a radioactive core wherein glass tube 22 has longitudinally opposing ends 27 which are open. By way of example only, an exemplary alternate embodiment brachytherapy implant seed 10*a* is shown in FIG. 2. Like numerals from the first embodiment have been utilized where appropriate, with differences being indicated with the suffix "a" or with different numerals. Inorganic amorphous silicate glass tube 22*a* comprises longitudinally opposing ends 27*a* that are sealed by inorganic amorphous silicate glass. Further in the depicted FIG. 2 embodiment, and by way of example only, materials 30*a* and 32*a* are also received over the ends 27*a* of inorganic amorphous silicate glass tube 22*a*.

Figure 3:
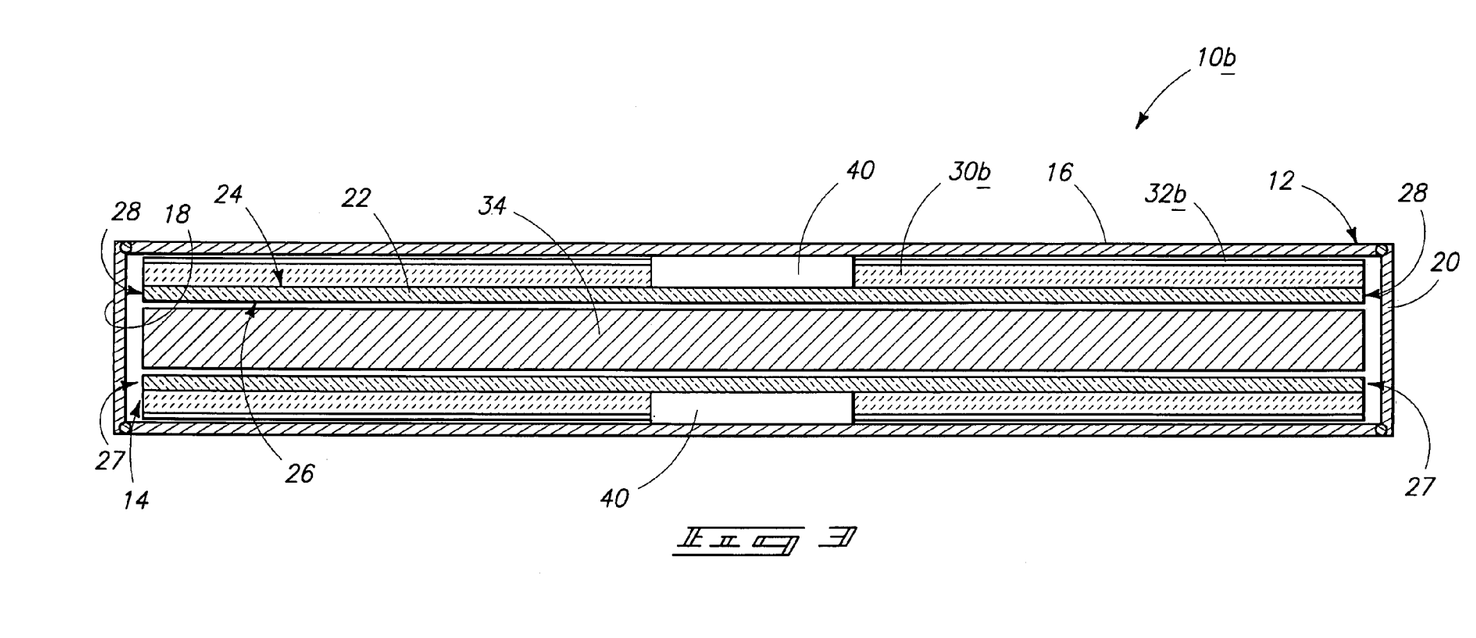
FIG. 3 is a diagrammatic sectional view of another alternate embodiment brachytherapy implant seed in accordance with an aspect of the invention.

The exemplary FIGS. 1 and 2 embodiments depict the inorganic crystalline ceramic coating 30/30*a* as coating all of tube exterior surface 24, and radioisotope 32/32*a* being received all along tube 22/22*a*. By way of example only, FIG. 3 illustrates an alternate embodiment brachytherapy implant seed 10*b*. Like numerals from the first described embodiment are utilized where appropriate, with differences being indicated with the suffix "b" or with different numerals. FIG. 3 depicts some center or core portion 40 which is either not coated with ceramic material or is effectively masked with a material that will not adsorb/absorb the radioisotope. Thereby, the therapeutic dose of radioactive material coats less than all of the tube exterior surface. Exemplary masking materials include polyacrylonitrile and waxes. In some implementations, such might be desirable to enhance uniform isotropy. An exemplary preferred length of region/portion 40 is from 1.0 mm to 4.0 mm, with such being centered relative to the length of metallic cylinder 12.

Figure 4:
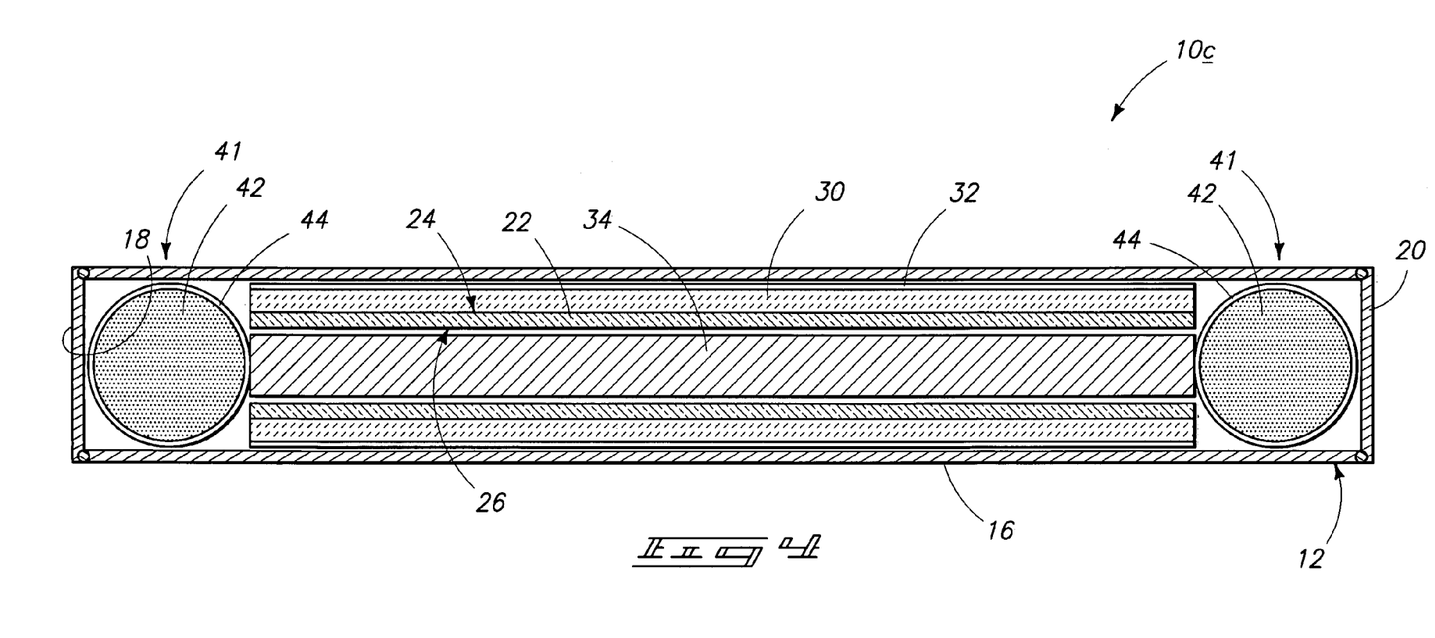
FIG. 4 is a diagrammatic sectional view of still another alternate embodiment brachytherapy implant seed in accordance with an aspect of the invention.

By way of example only, FIG. 4 depicts another exemplary embodiment. Like numerals from the first described embodiment have been utilized where appropriate, with differences being indicated with the suffix "c" or with different numerals. Brachytherapy implant seed 10*d* comprises a pair of balls 41 proximate the ends of inorganic metallic cylinder 12. Such might comprise radiographic marker material and/or more preferably comprise a therapeutic dose of radioactive material. By way of example only, such might comprise a radiopaque or ceramic core 42 having a therapeutic dose of radioactive material 44 received thereabout.

The above describes exemplary preferred brachytherapy implant seed embodiments independent of the method of manufacture. Described below are exemplary preferred methods of fabricating the above and other brachytherapy implant seeds in accordance with aspects of the invention, including methods of fabricating a brachytherapy implant seed core in accordance with aspects of the invention.

Figure 5:
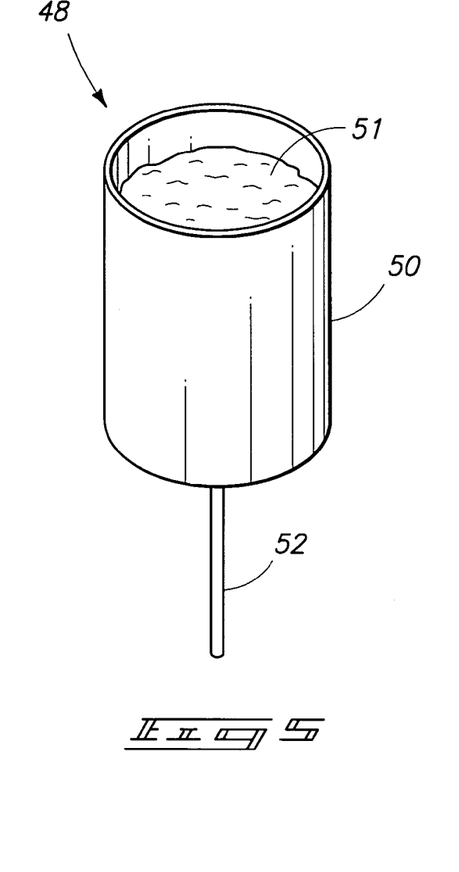
FIG. 5 is a perspective view of an exemplary apparatus useable in accordance with a methodical aspect of the invention.

In one implementation, a method of fabricating a brachytherapy implant seed core is described with reference to FIGS. 5 and 6. Such depict a suitable vessel 48 comprising a vessel body 50 and a die passageway 52. An exemplary volume for vessel body 50 is from 5 ml to 50 ml. Exemplary dimensions for die passageway 52 are 20 mm long, an outer diameter of 2.5 mm, and an inner diameter of 1 mm. A tube is provided which has an exterior surface extending axially along the tube. An exemplary tube material comprises inorganic amorphous silicate glass material, with tube 22 from the first described embodiment being a preferred example. Regardless, die passageway 52 is sized to slideably receive the tube therethrough to form a coating onto the tube exterior surface.

A mixture 51 of ceramic precursors is provided within vessel body 50. Exemplary ceramic precursors include any capable of providing the exemplary ceramic coatings provided above, for example a mixture of sodium silicate containing from about 10 weight percent to 40 weight percent aluminum oxide. In one exemplary embodiment, the mixture of ceramic precursors comprises an inorganic ion exchange material having an affinity for the radioactive material to be used subsequently. Exemplary preferred inorganic ion exchange materials include zeolites, and for example silicotitanate.

Figure 6:
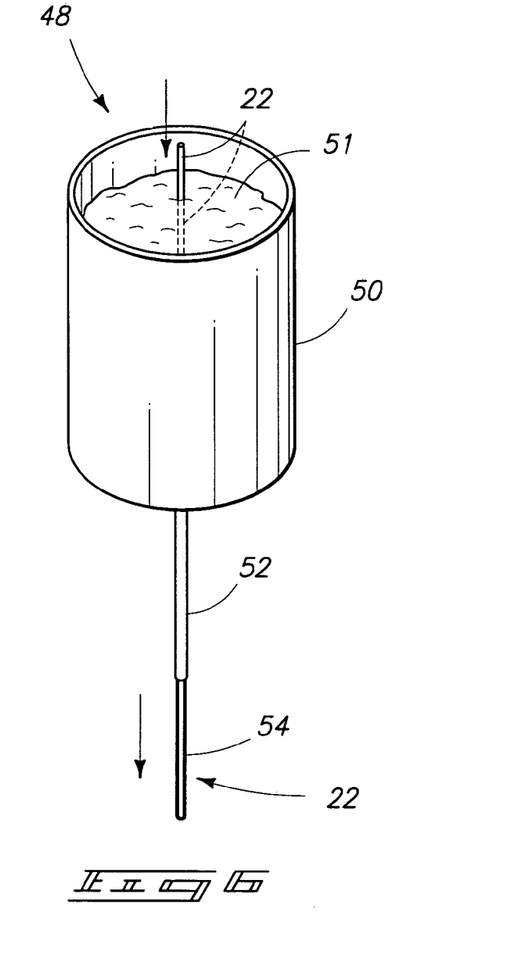
FIG. 6 is a view using the FIG. 5 apparatus used in accordance with an aspect of the invention.

Referring to FIG. 6, the tube (for example tube 22 from the first described embodiment) is moved into ceramic precursor mixture 51 within vessel body 50 and through die passageway 52 to outwardly of vessel 48 effective to form a coating 54 of the ceramic precursors onto the tube exterior surface. In reduction-to-practice examples, 100 mm lengths of 0.4 mm outer diameter by 0.3 mm inner diameter borosilicate glass tubing were utilized.

Thereafter, the ceramic precursor coating on the tube is exposed to a temperature effective to form an inorganic crystalline ceramic coating (for example coating 30 of the first described embodiment) over the tube exterior surface. In reduction-to-practice examples, the coated tubing is air dried and subsequently placed in a furnace. Such was then heated to 170° C. for approximately 60 minutes to convert the precursor coating to an inorganic crystalline ceramic coating which comprised sodium aluminosilicate. By way of example only, an exemplary temperature range to form the ceramic material is from 100° C. to 500° C. In reduction-to-practice examples, the coated glass tube was then measured for uniform thickness and cut into 4.0 mm to 4.25 mm lengths. Preferred attributes are otherwise as described above with respect to coated glass tube 22.

Thereafter, a therapeutic dose of radioactive material is sorbed onto the ceramic coating. One preferred manner of doing so is contacting the ceramic coated exterior surface with a solution comprising radioisotope ions having an affinity for the ceramic material and/or ion exchange material within the ceramic material. For example, and by way of example only, a highly purified and accurately known amount of radioactivity in solution (mCi/ml) can be transferred to ceramic coated cores by adsorption and/or absorption to the outer surfaces thereof by immersing the cores individually in 0.1 ml to 0.4 ml of solution for exemplary time periods of from 1 minute to 24 hours. Again, an exemplary preferred radiochemical is cesium-131. The solution and core are preferably gently agitated during the treatment time. A specific example solution comprised 0.25 ml of water containing 96.4 milliCuries of cesium-131 per ml for treating a single core, with the treatment time being 14.5 hours, and with the solution being at ambient room temperature and pressure conditions. Greater than 88% of the radioactivity was transferred to the core. The solution can be acid, base, aqueous or non-aqueous largely dependent upon the isotope and the ceramic material (including any ion exchange material, if any) that are utilized. The radioactive loaded cores are then removed from the solution, and preferably air-dried for one hour with the aid of a heat lamp.

Figure 7:
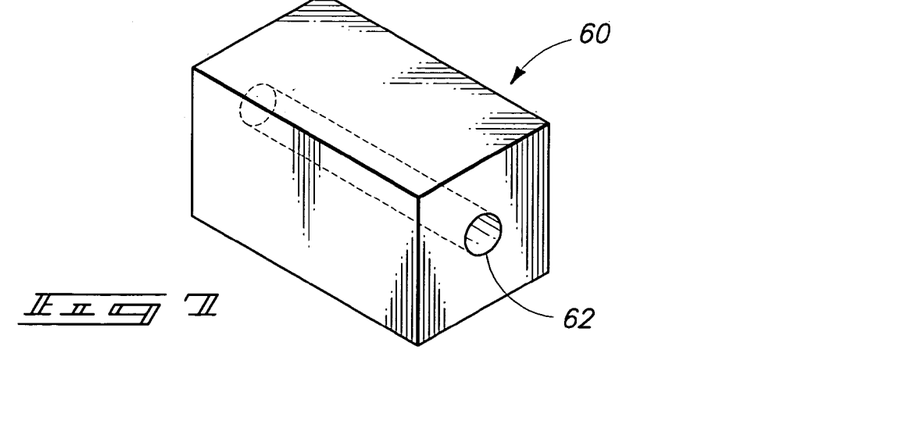
FIG. 7 is a perspective view of another exemplary apparatus useable in accordance with a methodical aspect of the invention.

The above provides but one exemplary described embodiment of a method of fabricating a brachytherapy implant seed core in accordance with exemplary methodical aspects of the invention. An additional method of fabricating a brachytherapy implant seed core comprises providing a tube having an exterior surface extending axially along the tube. Again preferably, the tube comprises an inorganic amorphous silicate glass material, for example tube 22 as described in the first embodiment. A mold is provided that comprises a mold cavity sized to receive the tube and form a coating thereover. By way of example only, FIG. 7 depicts a mold 60 having a mold cavity 62 formed therein. An exemplary manner of forming cavity 62 would be by drilling. Alternately, mold 60 might be comprised of two or more components/pieces which are assembled together to form mold body 60 with cavity 62. Regardless, the mold preferably has a melting temperature that is less than or equal to 500° C. Further and regardless, exemplary preferred mold materials comprise waxes (i.e., synthetic and/or natural waxes such as animal waxes, vegetable waxes and mineral waxes for example including petroleum waxes such as paraffin, microcrystalline, and petrolatum; and others) and plastics (i.e., polyethylenes, polyesters, polypropylenes, polyurethanes, polyvinyls, polycarbonates, nylons, acrylics, styrenes, and others).

A mixture of ceramic precursors is inserted within the mold cavity, and the tube is inserted within the mold cavity. Preferably, the ceramic precursor mixture is provided within the mold cavity first, followed by the tube, although the reverse order of insertion is also contemplated. An adherent coating of the ceramic precursors is formed onto the tube surface within the mold cavity, for example merely by allowing the ceramic precursors to cure onto the outer tube surface for some acceptable period of time, for example from one hour to twenty-four hours.

Thereafter, the mold is destructively melted, preferably melting the mold away from the ceramic precursor-coated tube, and even more preferably melting and vaporizing the mold material. An exemplary preferred heating temperature range for the melting is from 100° C. to 170° C. where the mold material at least has a melting temperature which is at or below 170° C. Any residual mold material can be dissolved in any suitable solvent, for example hexane for wax. After the melting, the ceramic precursor coating is exposed to a temperature effective to form an inorganic crystalline coating over the tube exterior surface, for example ceramic coating 30 in the above-described first embodiment. An exemplary preferred temperature range is as described in the preceding embodiment above, with a specific example being 170° C. and which will also tend to burn off any remaining wax or other molding material. After the exposing, a therapeutic dose of radioactive material is sorbed onto the ceramic coating, for example using any of the above-described or other methods. Note that with any of the above-described embodiments, the ceramic coating might be formed onto end surfaces and/or onto interior surfaces of the tube. Further, the tube longitudinally-opposing ends might be opened or sealed as inserted into the mold cavity. Further, an inorganic metallic marker might be provided within the tube. By way of example only and in accordance with this aspect of the invention, exemplary preferred tubes are from 0.69 mm to 0.70 mm in diameter. A preferred average thickness of the coating is 0.15 mm. At least where a radiographic marker in the form of a wire or rod is used, and in accordance with this particular embodiment, a preferred length is approximately 3.8 mm.

Aspects of the invention also contemplate methods of fabricating a brachytherapy implant seed. In one implementation, such comprises providing an inorganic amorphous silicate glass tube having an exterior surface extending axially along the tube. Preferred tubes are those described above in the first embodiment. At least a portion of the tube exterior surface is coated with ceramic precursors. Exemplary preferred manners are those described above, for example including the methods described in connection with FIGS. 5 and 6, and the methods described in connection with FIG. 7. However, any coating method is contemplated, whether existing or yet-to-be developed. By way of example only, preferred coating methods in addition to those of FIGS. 5-7 include aerosol spray, liquid spray, molding, die casting, non-aerosol microjet liquid spray, etc. Further, the ceramic precursors preferably have the preferred attributes as described above.

After the coating action, the ceramic precursors are exposed to a temperature effective to form a continuous inorganic crystalline ceramic coating from the precursors over the tube exterior surface portion. Exemplary preferred manners and temperatures for the exposing are as described above. Thereafter, a therapeutic dose of radioactive material is sorbed onto the ceramic coating. Preferred and exemplary manners of doing so are as described above.

At least a portion of the ceramic-coated glass tube with a therapeutic dose of radioactive material is provided within an inorganic metallic cylinder. An exemplary cylinder is cylinder 12 of the first described embodiment. Preferably, an exemplary such right cylinder has one of its ends open and the other end closed, for example by welding one of caps 18 and 20 onto cylinder portion 16. If an inorganic metallic radioactive marker in the form of a rod or wire is to be used or received within the ceramic-coated glass tube, such might be provided therein before or after insertion of the radioactive glass tube within the inorganic metallic cylinder. Such a radiographic marker might be crimped or otherwise cemented, or even just loosely received within the glass core.

Regardless, an inorganic metallic cap is ultimately welded onto an end of the inorganic metallic cylinder having the portion of the ceramic coated tube with therapeutic dose of radioactive material received therein. Preferred manners of welding are described below.

Specifically, a form of precision laser welding is preferably used as the sealing method for end caps 18, 20 such that a minimum amount of the preferred titanium metal is melted. Preferably, the welding techniques also produce a seed with a uniform thick wall about the seed towards minimizing attenuation of the radiation field and in achieving a substantially uniform distribution of the radiation. In a preferred method, a 0.10 mm thick end cap of approximately 0.81 mm diameter is stamped out of titanium sheet stock, and may produce edges that are "bottle cap" in appearance. Such can facilitate the end cap being seated on the cylindrical body immediately prior to welding. A preferred technique holds the end cap in place over/onto the cylindrical section with a carbide tip. The end cap is then tack welded at two locations approximately from 120° to 180° apart. The carbide tip is removed after the initial tack welding.

In one preferred implementation, the cap and cylinder are next rotated while firing a series of laser pulses towards the cap and cylinder effective to form a series of overlapping welds. Adjacent welds overlap one another by no more than 50% calculated as weld diameter overlap divided by weld diameter. More preferably, adjacent welds overlap one another by from 20% to 40%, and even more preferably from 20% to 30%, calculated as weld diameter overlap divided by weld diameter. A preferred effect, by way of example only and not by way of limitation, is to provide adequate weld overlap to obtain a good fluid tight seal while maintaining a mechanically strong seal capable of withstanding mechanical strength testing, for example tests ISO 9978:1992(E) and ISO 2919:1999(E).

Figure 8:
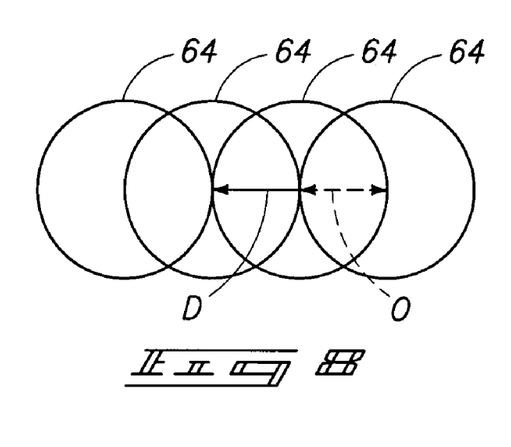
FIG. 8 is a diagrammatic depiction of weld overlap in accordance with an aspect of the invention.
Figure 9:
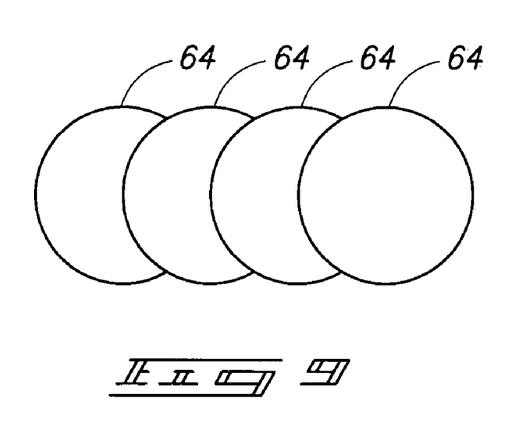
FIG. 9 is a diagrammatic depiction of weld overlap in accordance with an aspect of the invention.
Figure 10:
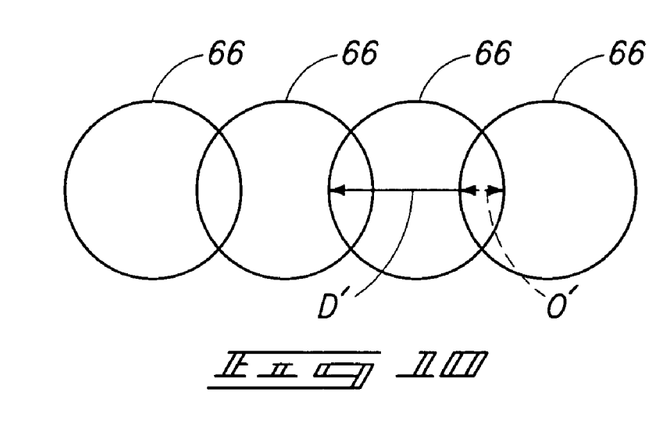
FIG. 10 is a diagrammatic depiction of weld overlap in accordance with an aspect of the invention.
Figure 11:
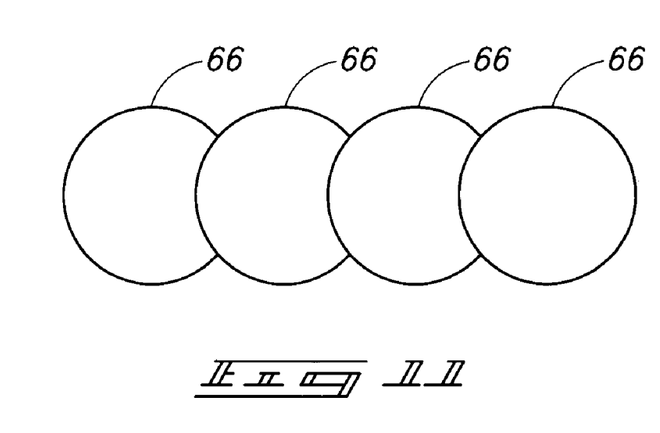
FIG. 11 is a diagrammatic depiction of weld overlap in accordance with an aspect of the invention.

FIGS. 8-11 diagrammatically depict exemplary laser weld overlaps, with FIGS. 8 and 9 depicting 50% overlap and FIGS. 10 and 11 depicting 25% overlap. FIGS. 8 and 10 diagrammatically depict the degrees of weld overlap, with FIGS. 9 and 11 diagrammatically depicting a finished appearance of the welds where such pulses are sequenced in time going from left to right, with each subsequent weld overlapping a portion of the preceding weld. Specifically, FIG. 8 depicts overlapping welds 64, with the third from the left depicted weld having a diameter D which is overlapped by the next adjacent weld by an overlap O which includes a portion of D. In the depicted FIGS. 8 and 9 example, O is 50% of D. Of course, the weld zone will likely not be perfectly circular, with the diameters referred to herein constituting an average diameter of immediately adjacent welds produced by the laser pulses.

FIGS. 10 and 11 depict a 25% overlap with respect to a series of overlapping welds 66. Accordingly, O' is 25% of diameter D in this example.

Figure 12:
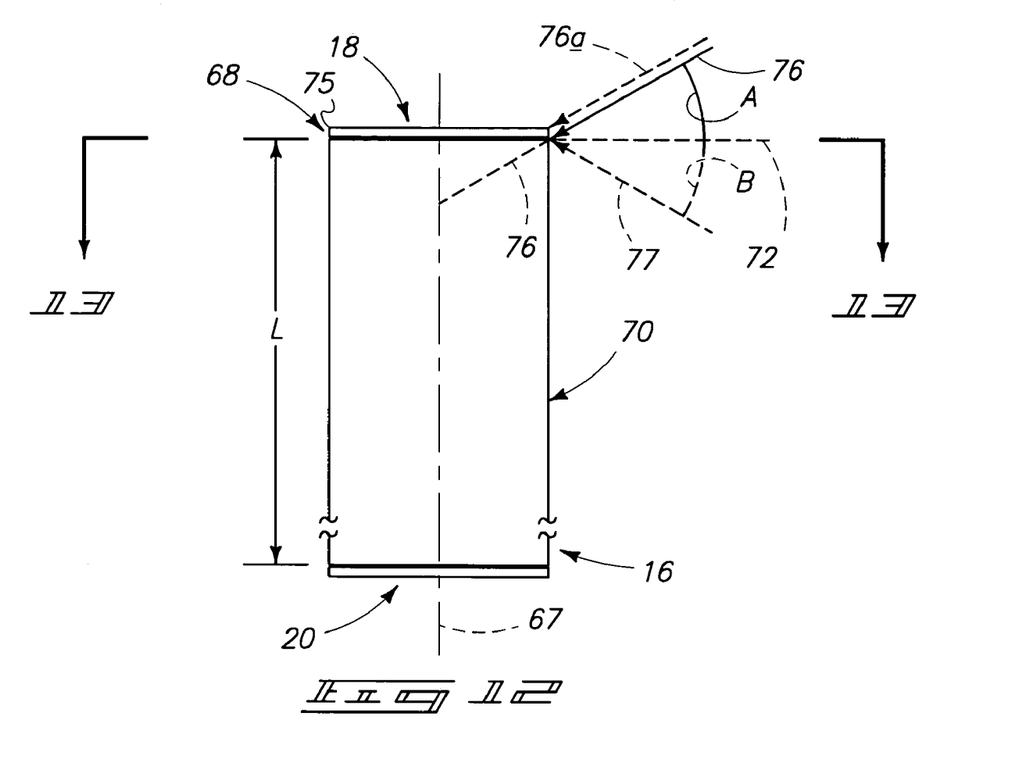
FIG. 12 is a diagrammatic depiction of a brachytherapy implant seed in fabrication in accordance an aspect of the invention.

Further preferably, the laser pulses are fired towards the cap and cylinder at a firing angle from perpendicular to an outer surface of the metallic cylinder. For example, FIG. 12 depicts inorganic metallic cylinder 16 having metal caps 18 and 20 received proximate opposing ends thereof Either or both of end caps 18 and 20 could be welded to inorganic metallic cylinder 16 in the manner being described. Inorganic metallic cylinder 16 can be considered as having a length L, a longitudinal axis 67, and an outer surface 70. Further, FIG. 12 depicts an exemplary interface 68 where metallic cap 18 meets or joins with metallic cylinder 16. Cap 18 has preferably been tack welded to cylinder 16 as described above. FIG. 12 also depicts an exemplary line 72 extending perpendicularly from outer surface 70 of metallic cylinder 16 proximate interface 68. A line 76 depicts an exemplary firing angle A from perpendicular line 72 for the laser pulses. Preferably, angle A is no greater than 30° from perpendicular to the outer surface of the metallic cylinder, more preferably from 15° to 30°, and most preferably from 18° to 22°.

Further preferably, the laser pulses are fired towards the cap and cylinder, for example along line 76, such that the firing angle (as depicted) is in a direction towards a majority of length L. Also contemplated, but considerably less preferred, would be directing laser pulses along a firing line 77 at a firing angle B which is in a direction away from the majority of length L of metallic cylinder 16. Further preferably, the inorganic metallic cap can be considered as having an outermost edge away from the inorganic metallic cylinder. Preferably, the welding comprises aiming respective centers of the laser pulses at locations which are more proximate to such outermost edge than to an interface of the cap and cylinder. In one preferred embodiment, the centers of the laser pulses are aimed at such outermost edge. For example, cap 18 can be considered as having such an outermost edge 75 extending about the upper periphery of cap 18 in the FIG. 12 orientation. Line 76*a* is an exemplary aiming line directed to upper edge 75 of cap 18.

Figure 13:
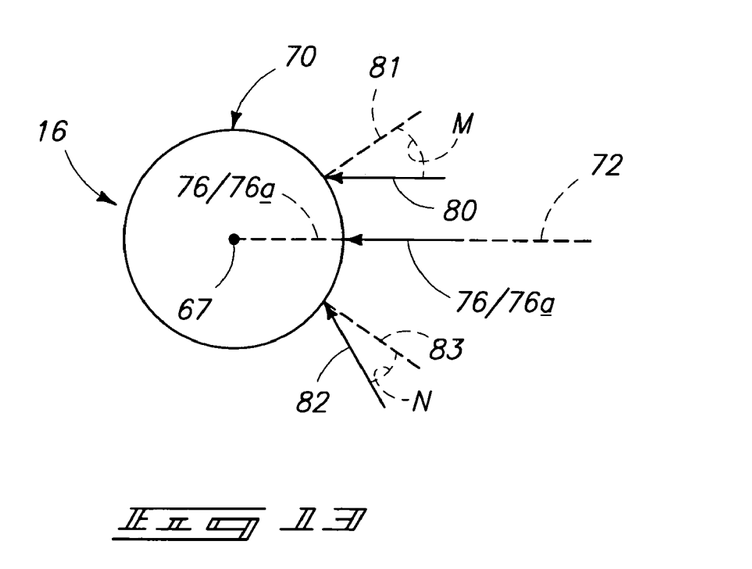
FIG. 13 is a diagrammatic depiction of a brachytherapy implant seed in fabrication in accordance an aspect of the invention, and is directed downwardly along line 13-13 in FIG. 12.

FIGS. 12 and 13 depict firing lines 76/76*a* (and accordingly, their firing angles from perpendicular) as being aligned to, and thereby extending to, longitudinal axis 67. FIG. 13 also depicts alternate exemplary firing lines 80 and 82. Such are still depicted as being angled from perpendiculars 81 and 83, respectively, from outer surface 70 by angles M and N, respectively, and may or may not be horizontally aligned relative to the FIG. 12 depicted orientation. Regardless, firing angles M and N are laterally spaced from longitudinal axis 67 such that the laser firing lines and angles do not extend to longitudinal axis 67, as occurs with respect to the illustrated firing lines and angles 76/76*a* and A.

Regardless, the welding preferably produces a series of circumferential welds about the metallic cylinder and cap, sealing the two together. By way of example only, an exemplary rotation speed for the metallic cylinder and cap is from 3 to 4 seconds for a complete rotation, with pulse energy and pulse intervals preferably selected to produce a weld spot every 0.17 mm to 0.25 mm about the circumference of the cylinder. The welding zone is preferably continuously purged with an inert gas, for example argon, for example at a flow rate of from 2 to 3 standard cubic feet per hour. Exemplary preferred weld parameters are selected to produce a tweld zone of approximately 0.20 mm to 0.35 mm diameter per pulse. An exemplary preferred pulse energy is 218 volts, with laser hits occurring at lengths of 3 milliseconds to 6 milliseconds, with the time between laser hits being approximately 300 milliseconds. Such exemplary preferred conditions utilizing a pulse overlap of 25%, firing angles at 18% to 22% from perpendicular as described, with the center of the pulse aimed at the upper edge of the end cap, resulted in and enabled the produced seeds to withstand an impact test wherein a steel hammer with a diameter of 1 inch and weighing 50 grams was dropped onto the seed from a height of 1 meter. After the impact, the seed was tested for leak tightness by immersion in hot water at a temperature of between 90° C. and 95° C. for 1 minute, with no air bubbles having been formed on the outside of the seed.

The above describes but preferred techniques of welding in accordance with certain aspects of the invention. Yet, aspects of the invention further encompass methods of fabricating a brachytherapy implant seed utilizing one or a combination of the variously above-stated preferred exemplary welding attributes. In accordance with one implementation, a method of fabricating a brachytherapy implant seed comprises providing an inorganic metallic cylinder. An inorganic metallic cap is welded onto an end of the inorganic metallic cylinder. The welding comprises firing a series of laser pulses towards the cap and cylinder while rotating the cap and cylinder effective to form a series of overlapping welds. In one implementation, adjacent welds overlap one another by no more than 50% calculated as weld diameter overlap divided by weld diameter. In one implementation, the laser pulses are fired towards the cap and cylinder at a firing angle from perpendicular to an outer surface of the metallic cylinder. A radioactive core is provided within the inorganic metallic cylinder, with such core comprising a therapeutic dose of radioactive material. The radioactive core might be provided within the inorganic metallic cylinder before or after the welding, as well as the welding occurring with respect to both caps to opposing ends of the inorganic metallic cylinder. Radioactive core fabrication and other attributes with respect to the design and manufacture are preferably as described in the above embodiments, although in no way being required in accordance with these latter aspects of the invention as just so literally stated.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A brachytherapy implant seed comprising:
    a sealed inorganic metallic cylinder having a radioactive core received therein, the radioactive core comprising:
        an inorganic amorphous silicate glass tube having an exterior surface extending axially along the tube; and
        an inorganic crystalline ceramic coating received on at least a portion of the inorganic amorphous glass tube exterior surface, said coating comprising a therapeutic dose of radioactive material; and a radiographic marker received within the sealed inorganic metallic cylinder.

2. The brachytherapy implant seed of claim 1 wherein the glass comprises borosilicate.

3. The brachytherapy implant seed of claim 1 wherein the glass comprises phosphosilicate.

4. The brachytherapy implant seed of claim 1 wherein the inorganic crystalline ceramic comprises a metal silicate.

5. The brachytherapy implant seed of claim 4 wherein the inorganic crystalline ceramic comprises an aluminosilicate.

6. The brachytherapy implant seed of claim 1 wherein the therapeutic dose of radioactive material coats all of the tube exterior surface.

7. The brachytherapy implant seed of claim 1 wherein the therapeutic dose of radioactive material coats less than all of the tube exterior surface.

8. The brachytherapy implant seed of claim 7 wherein the therapeutic dose of radioactive material does not coat from 1.0 mm to 4.0 mm of a longitudinal central portion of the tube.

9. The brachytherapy implant seed of claim 1 wherein the inorganic crystalline ceramic coating has a thickness of from 0.1 mm. to 0.4 mm.

10. The brachytherapy implant seed of claim 1 wherein the inorganic crystalline ceramic coating has a thickness which is substantially the same as that of the inorganic amorphous silicate glass tube.

11. The brachytherapy implant seed of claim 1 wherein the inorganic crystalline ceramic coating has a thickness which is greater than that of the inorganic amorphous silicate glass tube.

12. The brachytherapy implant seed of claim 1 wherein the inorganic crystalline ceramic coating has a thickness which is less than that of the inorganic amorphous silicate glass tube.

13. The brachytherapy implant seed of claim 1 wherein the inorganic amorphous silicate glass tube comprises longitudinally opposing ends which are sealed by inorganic amorphous silicate glass.

14. The brachytherapy implant seed of claim 1 wherein the radiographic marker is received within the inorganic amorphous silicate glass tube.

15. The brachytherapy implant seed of claim 1 comprising a pair of balls received within longitudinal ends of the sealed inorganic metallic cylinder.

16. The brachytherapy implant seed of claim 15 wherein the balls comprise radiographic marker material.

17. The brachytherapy implant seed of claim 15 wherein the balls comprise a therapeutic dose of radioactive material.

18. The brachytherapy implant seed of claim 15 wherein the balls comprise an inorganic crystalline ceramic coated with a therapeutic dose of radioactive material.

19. A brachytherapy implant seed comprising:

a sealed inorganic metallic cylinder;

a tubular core received within the sealed inorganic metallic cylinder and having an inner layer and a outer layer, the inner layer comprising an inorganic amorphous silicate glass tube having an exterior surface extending along a length of the glass tube, and the outer layer comprising an inorganic crystalline ceramic received on at least a portion of the exterior surface of the inner layer;

a therapeutic dose of radioactive material applied to at least a portion of the outer layer of the tubular core; and a radiographic marker received within the sealed inorganic metallic cylinder.

20. The brachytherapy implant seed of claim 19 wherein the outer layer of the tubular core is received on an entire length of the exterior surface of the inner layer of the tubular core.

21. The brachytherapy implant seed of claim 19 wherein the outer layer of the tubular core is received on less than the entire length of the exterior surface of the first layer of the tubular core.

22. The brachytherapy implant seed of claim 19 wherein the therapeutic dose of radioactive material is applied to an entire outer surface of the outer layer of the tubular core.

23. The brachytherapy implant seed of claim 19 wherein the therapeutic dose of radioactive material is applied to less than the entire outer surface of the outer layer of the tubular core.

24. The brachytherapy implant seed of claim 23 wherein the therapeutic dose of radioactive material is not applied to a 1.0 mm to 4.0 mm longitudinal central portion of the outer surface of the outer layer of the tubular core.

25. The brachytherapy implant seed of claim 19 wherein the outer layer of the tubular core has a thickness of from 0.1 mm. to 0.4 mm.

26. The brachytherapy implant seed of claim 19 wherein the outer layer of the tubular core has a thickness which is substantially the same as that of the inner layer of the tubular core.

27. The brachytherapy implant seed of claim 19 wherein the outer layer of the tubular core has a thickness which is greater than that of the inner layer of the tubular core.

28. The brachytherapy implant seed of claim 19 wherein the outer layer of the tubular core has a thickness which is less than that of the inner layer of the tubular core.

* * * * *